US011376111B2

(12) United States Patent
Walsh et al.

(10) Patent No.: US 11,376,111 B2
(45) Date of Patent: Jul. 5, 2022

(54) PANCREATIC STENT WITH DRAINAGE FEATURE

(71) Applicant: BOSTON SCIENTIFIC SCIMED, INC., Maple Grove, MN (US)

(72) Inventors: Kevin Walsh, Wellesly, MA (US); Gary Trendel, Hopkinton, MA (US); Paul Mannion, Shrewsbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 296 days.

(21) Appl. No.: 16/706,225

(22) Filed: Dec. 6, 2019

(65) Prior Publication Data

US 2020/0107924 A1 Apr. 9, 2020

Related U.S. Application Data

(63) Continuation of application No. 15/819,428, filed on Nov. 21, 2017, now Pat. No. 10,500,035, which is a continuation of application No. 14/878,050, filed on Oct. 8, 2015, now Pat. No. 9,839,508.

(60) Provisional application No. 62/061,782, filed on Oct. 9, 2014.

(51) Int. Cl.
| | | |
|---|---|---|
| *A61F 2/04* | (2013.01) | |
| *A61F 2/07* | (2013.01) | |
| *A61F 2/90* | (2013.01) | |
| *A61M 27/00* | (2006.01) | |

(52) U.S. Cl.
CPC ............. *A61F 2/04* (2013.01); *A61F 2/07* (2013.01); *A61F 2/90* (2013.01); *A61M 27/002* (2013.01); *A61F 2002/041* (2013.01); *A61F 2002/072* (2013.01); *A61F 2240/001* (2013.01)

(58) Field of Classification Search
CPC ...... A61F 2/04; A61F 2/07; A61F 2/90; A61F 2240/001; A61F 2210/0014; A61L 31/022
USPC ........................................................ 623/1.11
See application file for complete search history.

(56) References Cited

U.S. PATENT DOCUMENTS

| | | |
|---|---|---|
| 3,938,529 A | 2/1976 | Gibbons |
| 5,238,004 A | 8/1993 | Sahatjian et al. |
| 5,383,927 A | 1/1995 | De Goicoechea et al. |
| 5,607,464 A | 3/1997 | Trescony et al. |
| 5,653,745 A | 8/1997 | Trescony et al. |
| 5,697,970 A | 12/1997 | Schmitt et al. |
| 5,876,450 A | 3/1999 | Johlin, Jr. |
| 5,984,965 A | 11/1999 | Knapp et al. |
| 6,132,471 A | 10/2000 | Johlin, Jr. |

(Continued)

FOREIGN PATENT DOCUMENTS

| | | |
|---|---|---|
| EP | 2537491 A1 | 12/2012 |
| JP | 2012515637 A | 7/2012 |

(Continued)

*Primary Examiner* — Suzette J Gherbi
(74) *Attorney, Agent, or Firm* — Seager, Tufte & Wickhem, LLP

(57) ABSTRACT

A pancreatic stent includes a main body convertible between a compressed configuration for delivery and an expanded configuration once deployed, the main body including an inner surface defining a stent lumen and an outer surface. A plurality of drainage features are formed within the outer surface of the main body, the plurality of drainage features permitting placement of the pancreatic stent within a patient's pancreas without blocking side branches of the pancreas.

18 Claims, 4 Drawing Sheets

(56) References Cited

U.S. PATENT DOCUMENTS

| | | |
|---|---|---|
| 6,221,060 B1 | 4/2001 | Willard |
| 6,258,117 B1 | 7/2001 | Camrud et al. |
| 6,358,275 B1 | 3/2002 | McIlroy et al. |
| 6,416,537 B1 | 7/2002 | Martakos et al. |
| 6,451,052 B1 | 9/2002 | Burmeister et al. |
| 6,508,803 B1 | 1/2003 | Horikawa et al. |
| 6,709,451 B1 | 3/2004 | Noble et al. |
| 7,118,600 B2 | 10/2006 | Dua et al. |
| 7,195,646 B2 | 3/2007 | Nahleili |
| 7,314,489 B2 | 1/2008 | McKenna et al. |
| 7,338,530 B2 | 3/2008 | Carter et al. |
| 7,670,367 B1 | 3/2010 | Chouinard et al. |
| 7,909,797 B2 | 3/2011 | Kennedy, II et al. |
| 7,967,830 B2 | 6/2011 | Ayala et al. |
| 8,221,505 B2 | 7/2012 | Skerven |
| 8,435,283 B2 | 5/2013 | Jordan et al. |
| 8,459,164 B2 | 6/2013 | Lilburn et al. |
| 8,603,185 B2 | 12/2013 | Shah et al. |
| 9,839,508 B2 * | 12/2017 | Walsh ..................... A61F 2/07 |
| 10,500,035 B2 * | 12/2019 | Walsh ................. A61M 27/002 |
| 10,947,651 B2 * | 3/2021 | Lilburn ..................... A61F 2/90 |
| 2002/0179166 A1 | 12/2002 | Houston et al. |
| 2003/0093145 A1 | 5/2003 | Lawrence-Brown et al. |
| 2005/0033418 A1 | 2/2005 | Banas et al. |
| 2005/0096733 A1 * | 5/2005 | Kovneristy ............... A61F 2/90 |
| | | 623/1.22 |
| 2005/0283962 A1 | 12/2005 | Boudjemline |
| 2006/0265051 A1 | 11/2006 | Caro et al. |
| 2007/0123969 A1 | 5/2007 | Gianotti |
| 2008/0228262 A1 | 9/2008 | Goldmann et al. |
| 2008/0319540 A1 | 12/2008 | Jordan et al. |
| 2009/0030363 A1 | 1/2009 | Gellman |
| 2009/0061072 A1 * | 3/2009 | Isch ..................... B05D 1/02 |
| | | 427/2.25 |
| 2009/0198315 A1 | 8/2009 | Boudjemline |
| 2009/0276029 A1 | 11/2009 | Caro et al. |
| 2010/0030321 A1 | 2/2010 | Mach |
| 2010/0100170 A1 | 4/2010 | Tan et al. |
| 2010/0145467 A1 | 6/2010 | Davoudi et al. |
| 2010/0191319 A1 | 6/2010 | Lilburn et al. |
| 2010/0211098 A1 | 8/2010 | Hadba et al. |
| 2010/0256731 A1 | 10/2010 | Mangiardi |
| 2013/0269506 A1 * | 10/2013 | Lilburn ..................... D04C 1/06 |
| | | 87/9 |
| 2014/0243992 A1 | 8/2014 | Walsh et al. |
| 2014/0277561 A1 | 9/2014 | Jordan |
| 2014/0343683 A1 | 11/2014 | Jeon et al. |
| 2015/0105852 A1 * | 4/2015 | Noffke ..................... A61F 2/82 |
| | | 623/1.16 |
| 2016/0302910 A1 | 10/2016 | Jordan |
| 2019/0015230 A1 | 1/2019 | Walsh et al. |
| 2019/0053921 A1 | 2/2019 | Mangiardi |
| 2019/0216621 A1 * | 7/2019 | Lilburn ..................... D04C 3/14 |
| 2020/0155732 A1 * | 5/2020 | Rangwala ............... A61L 31/18 |
| 2021/0172102 A1 * | 6/2021 | Lilburn ..................... A61F 2/90 |
| 2021/0236309 A1 * | 8/2021 | Folan ..................... A61F 2/885 |

FOREIGN PATENT DOCUMENTS

| | | |
|---|---|---|
| KR | 1020110003886 A | 1/2011 |
| WO | 0236047 A1 | 5/2002 |
| WO | 2014134352 A1 | 9/2014 |
| WO | 2014164308 A1 | 10/2014 |

* cited by examiner

PANCREATIC STENT WITH DRAINAGE FEATURE

CROSS-REFERENCE TO RELATED APPLICATIONS

This application is a continuation of U.S. application Ser. No. 15/819,428, filed Nov. 21, 2017, which is a continuation of U.S. application Ser. No. 14/878,050, filed Oct. 8, 2015, now U.S. Pat. No. 9,839,508, which claims priority under 35 U.S.C. § 119 to U.S. Provisional Application Ser. No. 62/061,782, filed Oct. 9, 2014, the entirety of which is incorporated herein by reference.

TECHNICAL FIELD

The disclosure is directed to an endoprosthesis, such as a stent. More particularly, the disclosure is directed to a pancreatic stent including drainage features formed within an outer surface of the pancreatic stent.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. In some instances, an endoprosthesis may be used within an organ such as the pancreas or in the biliary system. In application such as the pancreas, there can be a desire to retain patency within a main lumen within the pancreas while not blocking fluid flow from side branches within the pancreas.

Accordingly, it is desirable to provide endoprostheses that can retain patency within a main lumen within the body structure (e.g., the pancreas) while not blocking fluid flow from side branches within the body structure (e.g., the pancreas).

BRIEF SUMMARY

The disclosure is directed to several alternative designs, materials and methods of manufacturing medical device structures and assemblies, and uses thereof.

In one example, a medical stent, such as a pancreatic stent, includes a main body convertible between a compressed configuration for delivery and an expanded configuration once deployed, the main body including an inner surface defining a stent lumen and an outer surface. A plurality of drainage features are formed within the outer surface of the main body, the plurality of drainage features permitting placement of the medical stent within a patient's body structure (e.g., pancreas) without blocking side branches of the body structure (e.g., pancreas).

Alternatively, or additionally, the main body includes an expandable metal framework.

Alternatively, or additionally, the medical stent further includes a polymeric layer over the expandable metal framework, the expandable metal framework and the polymeric layer in combination convertible between the compressed configuration and the expanded configuration.

Alternatively, or additionally, the expandable metal framework includes a braided metal structure.

Alternatively, or additionally, the braided metal structure includes nitinol.

Alternatively, or additionally, and in the compressed configuration, the medical stent has a diameter of at least about 2 millimeters.

Alternatively, or additionally, and in the expanded configuration, the medical stent has a diameter in the range of about 4 to about 24 millimeters.

In another example, a medical stent, such as a pancreatic stent, includes an expandable metal support structure that is convertible between a compressed configuration for delivery and an expanded configuration once deployed. A polymeric covering is disposed over the expandable metal support structure, the polymeric covering expandable with the expandable metal support structure. A plurality of drainage features are formed in the medical stent, the plurality of drainage features permitting placement of the medical stent within a patient's body structure (e.g., pancreas) without blocking side branches of the body structure (e.g., pancreas).

Alternatively, or additionally, the expandable metal support structure includes a braided metal stent formed having a high-low pattern in at least some adjoining windings.

Alternatively, or additionally, the polymeric covering conforms to the high-low pattern in at least some of the adjoining windings to form the plurality of drainage features.

Alternatively, or additionally, the braided metal stent is formed from nitinol wire.

Alternatively, or additionally, the high-low pattern is formed by braiding the braided metal stent on a mandrel having a high-low pattern formed on an outer surface of the mandrel.

Alternatively, or additionally, at least some of the plurality of drainage features extend helically about the medical stent.

In another example, a method of manufacturing an expandable medical stent including drainage features includes using a mandrel having a high-low pattern formed within an outer surface of the mandrel to braid an expandable metal support structure having a high-low pattern in at least some adjacent windings. The expandable metal support structure is removed from the mandrel. A polymeric layer is formed over the expandable metal support structure and conforms to the high-low pattern of the expandable metal support structure to form the drainage features.

Alternatively, or additionally, using a mandrel having a high-low pattern includes using a mandrel having a herringbone pattern of channels including a first plurality of channels extending helically in a first direction and a second plurality of channels extending helically in a second direction.

Alternatively, or additionally, removing the expandable metal support structure from the mandrel includes applying a compressive axial force to the expandable metal support structure to shorten its length and thus increase its diameter.

Alternatively, or additionally, the expandable metal support structure is braided from a wire formed of a shape memory material, and removing the expandable metal support structure from the mandrel includes utilizing its shape memory properties to increase its diameter.

Alternatively, or additionally, the wire formed of a shape memory material includes nitinol.

Alternatively, or additionally, forming a polymeric layer over the expandable metal support structure includes stretching a polymeric sleeve over the expandable metal support structure.

Alternatively, or additionally, the polymeric layer includes silicone.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
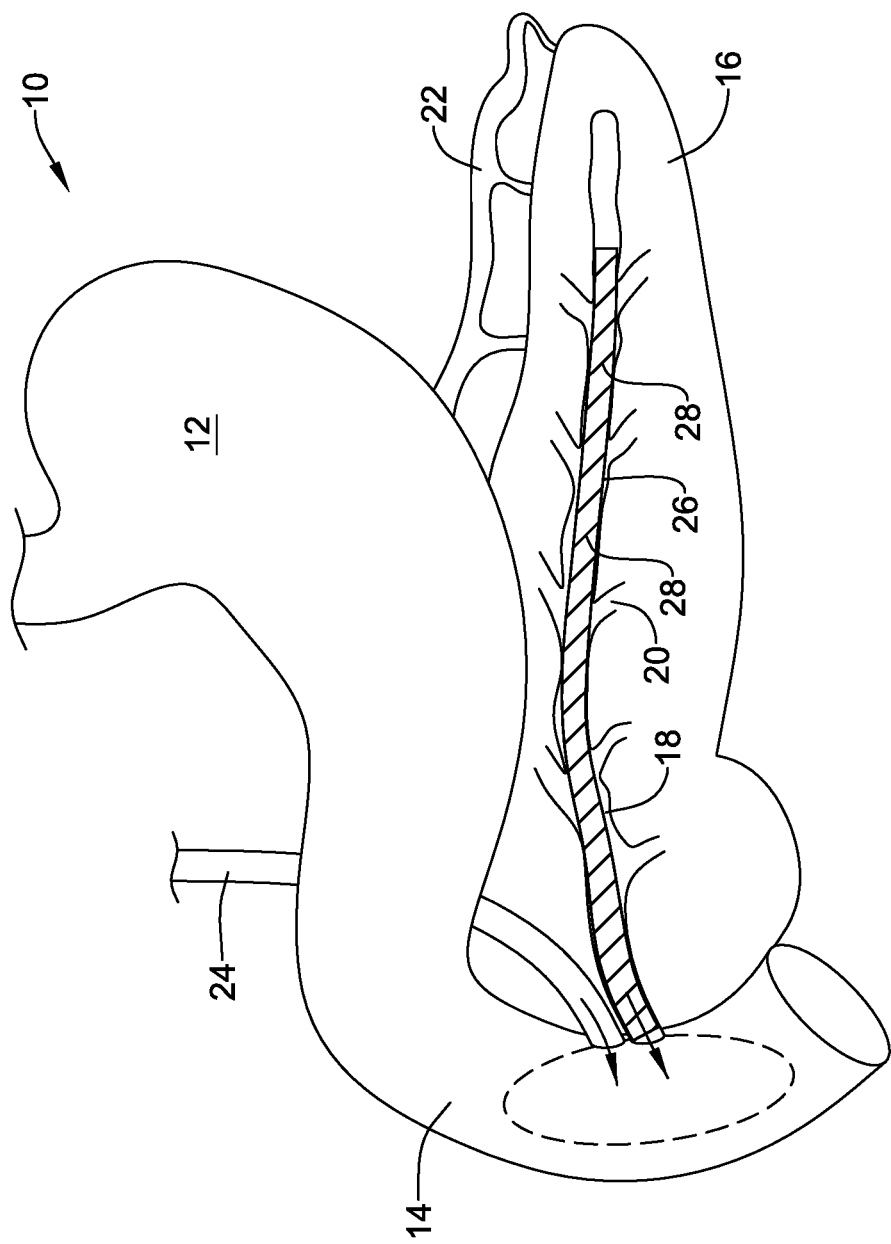
FIG. 1 is a schematic illustration of a portion of a patient's digestive system, including stomach and pancreas, illustrating placement of a pancreatic stent in accordance with an embodiment of the disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 provides a schematic illustration of a portion of a patient's digestive system 10, including a stomach 12 and duodenum 14. The patient's pancreas 16 is located just below the stomach 12 and is shown in cutaway fashion, illustrating the main pancreatic duct 18 extending through the pancreas 16 and terminating within the duodenum 14. The main pancreatic duct 8 is in fluid communication with a plurality of side branches 20 within the pancreas 16. While not expressly illustrated, the pancreas 16 includes duct cells that secrete aqueous $NaHCO_3$ solution into the main pancreatic duct 18. The pancreas 16 also includes Acinar cells that secrete digestive enzymes into the main pancreatic duct 18. While not illustrated, the pancreas 16 also includes Islets of Langerhans, which produce hormones such as insulin and glucagon. These hormones are excreted by the pancreas 16 into the blood stream, indicated as blood vessel 22, and the hormones then enter the stomach 12. A bile duct 24 extends from the liver (not shown) and also outputs into the duodenum 14.

In some instances, the main pancreatic duct 18 may become narrowed or inflamed, and there may be a desire to maintain the patency of the main pancreatic duct 18. In some embodiments, as illustrated, an endoprosthesis 26 may be deployed within the main pancreatic duct 18. The endoprosthesis 26 may be implanted in any suitable manner, including reaching the interior of the main pancreatic duct 18 from the interior of the duodenum 14. As will be discussed with respect to subsequent drawings, the endoprosthesis 26 may include a plurality of drainage features 28. The drainage features 28 may permit fluids exiting the side branches 20 and flow into the main pancreatic duct 18 and thus from there into the duodenum 14.

It will also be appreciated that while the endoprosthesis 26 is illustrated and described herein as a pancreatic stent 26, the endoprosthesis 26 may be deployed in a variety of other bodily lumens, including but not limited to the vascular, urinary, biliary, tracheobronchial, esophageal or renal tracts. Although illustrated as a stent, the endoprosthesis 26 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

Figure 2:
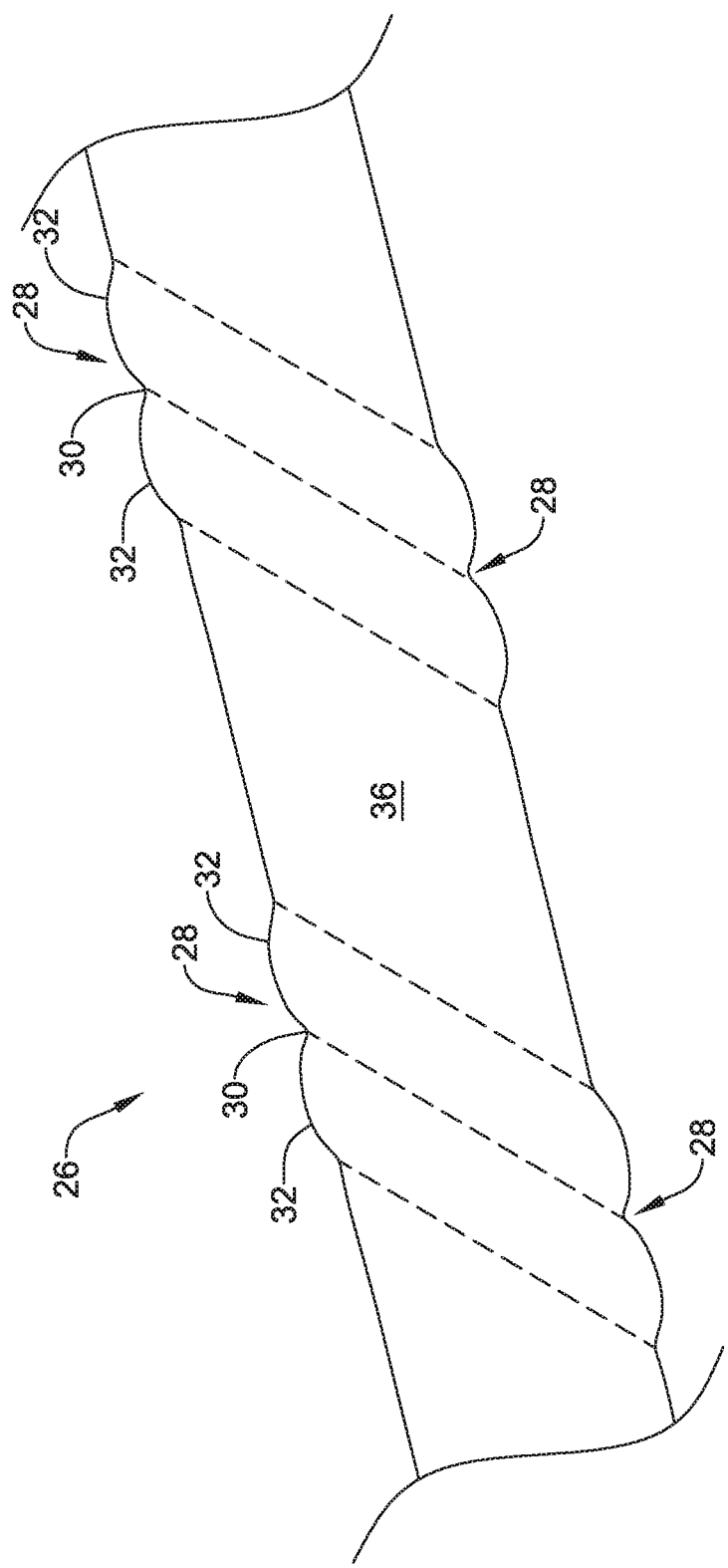
FIG. 2 is a schematic illustration of a pancreatic stent including drainage features in accordance with an embodiment of the disclosure.

Referring to FIG. 2, the pancreatic stent 26 may be seen as including several drainage features 28. Each of the drainage features 28 may be considered as including a valley 30 defined between peaks 32 on either side of the valley 30. In some embodiments, as can be seen in phantom, the drainage features 28 may wrap helically at least partway around the circumference of the pancreatic stent 26. As can be seen from FIGS. 2 and 3, the pancreatic stent 26 includes an expandable support structure 34 (FIG. 3), such as an expandable metal support structure, and a polymeric layer or covering 36 (FIG. 2) disposed over the expandable support structure 34.

The peaks 32 may extend radially outward from the central longitudinal axis further than the valley 30 between the peaks 32. In some embodiments, the peaks 32 may extend a distance above the valley 30 that ranges from about 5 percent to about 15 percent, or in some cases about 10 percent, of an overall diameter of the pancreatic stent 26. It will be appreciated that the peaks 32 and valleys 30 are formed as a result of the high-low pattern of the underlying expandable support structure 34. In some embodiments, the distance between the peak 32 and the adjoining valley 30 may be considered in terms of the diameter of the wire used to form the expandable support structure 34. In some embodiments, the peak to valley distance may be about three times or more of the wire diameter, about four times or more of the wire diameter, or about five times or more of the wire diameter, for example.

In some instances, the valley 30 between the peaks 32 of a drainage feature 28 may be located at substantially the same radial distance as the outer diameter of the pancreatic stent 26 between drainage features 28. However, in other instances, the valley 30 between the peaks 32 of a drainage feature 28 may be located at substantially radially outward from or radially inward from the outer diameter of the pancreatic stent 26 between drainage features 28.

It will be appreciated that the pancreatic stent 26 can have a compressed configuration for delivery and a larger, expanded configuration once implanted. In some embodiments, the pancreatic stent 26 may have a compressed diameter that is about 1 millimeter to about 6 millimeters, about 2 millimeters to about 6 millimeters, or about 2 millimeters to about 4 millimeters, for example. In some embodiments, the pancreatic stent 26 may have an expanded diameter that is in the range of about 4 millimeters to about 24 millimeters, about 4 millimeters to about 20 millimeters, about 4 millimeters to about 16 millimeters, about 4 millimeters to about 12 millimeters, about 6 millimeters to about 20 millimeters, about 6 millimeters to about 16 millimeters, or about 6 millimeters to about 12 millimeters, for example.

In some embodiments, the pancreatic stent 26 may have a compressed diameter that is about 25 percent or less, about 33 percent or less, or about 50 percent or less than its expanded diameter. For example, the pancreatic stent 26 may have the following compressed and expanded diameters.

| Stent Expanded Diameter (millimeters) | Stent Compressed Diameter ≤25% of Expanded (millimeters) | Stent Compressed Diameter ≤33% of Expanded (millimeters) | Stent Compressed Diameter ≤50% of Expanded (millimeters) |
| --- | --- | --- | --- |
| 4 | ≤1 | ≤1.33 | ≤2 |
| 8 | ≤2 | ≤2.67 | ≤4 |
| 12 | ≤3 | ≤4 | ≤6 |
| 16 | ≤4 | ≤5.33 | ≤8 |
| 20 | ≤5 | ≤6.67 | ≤10 |
| 24 | ≤6 | ≤8 | ≤12 |

Figure 3:
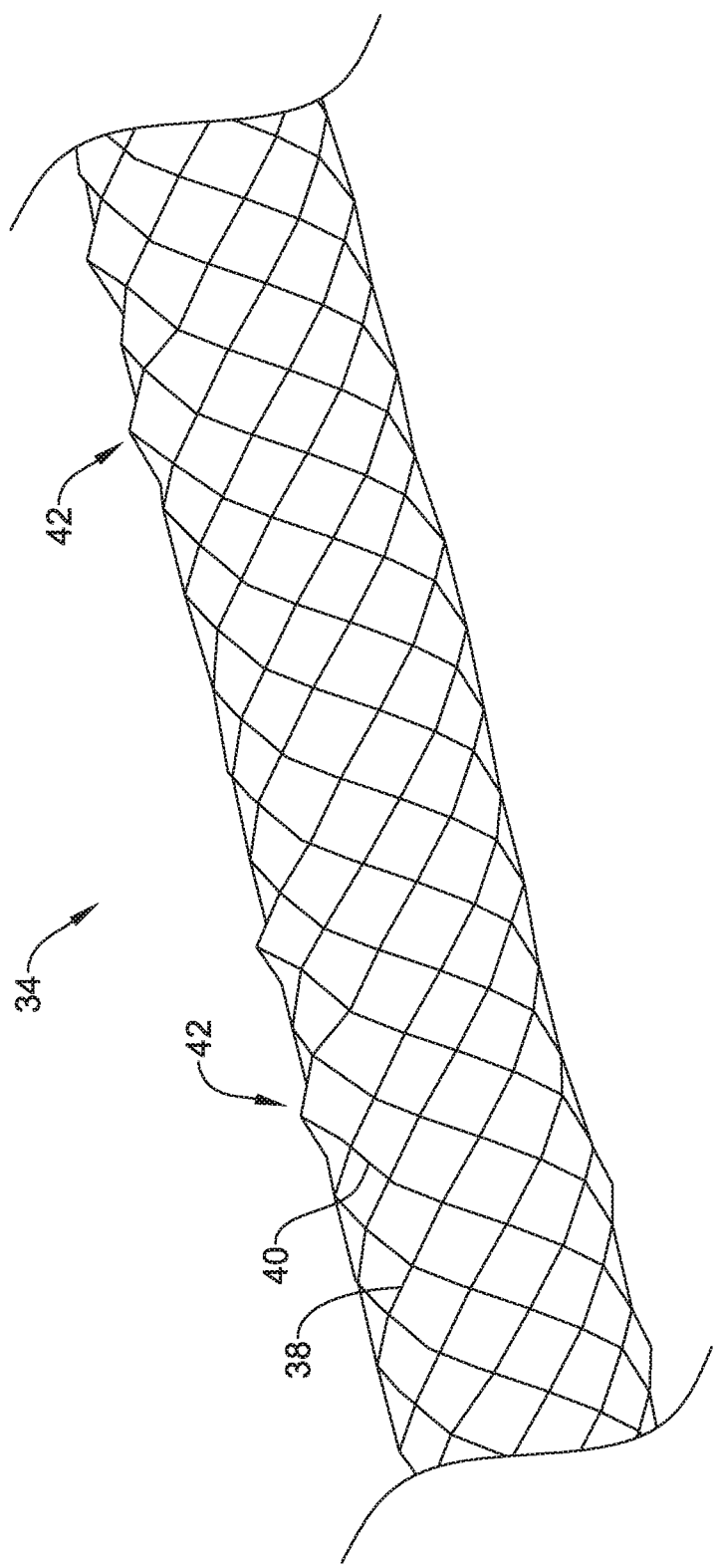
FIG. 3 is a schematic illustration of the metal framework of the pancreatic stent of FIG. 2, in accordance with an embodiment of the disclosure.

FIG. 3 provides an illustration of the expandable metal support structure 34. It can be seen that the expandable metal support structure 34 may be considered as being a braided or woven stent, in some instances. In other instances, the expandable metal support structure 34 may be otherwise formed of one or more, or a plurality of wire filaments wound and/or interwoven into a tubular construct, for example. In some embodiments, the expandable metal support structure 34 may be braided or otherwise formed from a shape memory material such as a Nitinol wire. As with any braid, the expandable metal support structure 34 may include one or more interwoven wires, such as one or more wires 38 that extend helically in a first direction and one or more wires 40 that wrap over and under the one or more wires 38 and that extend helically in a second direction that is generally opposite the first direction.

In some embodiments, as generally indicated at position 42 in FIG. 3, it can be seen that the one or more wires 38 and the one or more wires 40 generally stand above (e.g., extend radially outward from) where the one or more wires 38 and the one or more wires 40 generally define the expandable metal support structure 34. The one or more wires 38 and the one or more wires 40, in combination, may be considered as forming a high-low pattern in which a winding of the one or more wires 38, 40 may be relatively higher or lower than an adjacent winding. In other words, the high-low pattern formed with the interwoven wires 38, 40 may result in portions of the wires 38, 40 extending radially outward from the central axis of the expandable metal support structure 34 further than other portions of the wires 38, 40.

In some instances, one of the wires 40 (helically wound in the same helical direction as the peaks 32) may follow a peak 32 helically around the circumference of the pancreatic stent 26, while another of the wires 40 (helically wound in the same helical direction as the peaks 32) may follow an adjacent peak 32 of a drainage feature 28 helically around the circumference of the pancreatic stent 26. In some instances, another wire 40 (helically wound in the same helical direction as the peaks 32) may follow a valley 30 helically around the circumference of the pancreatic stent 26 between adjacent wires 40 helically following the adjacent peaks 32.

The wires 38 (helically wound in an opposite helical direction as the peaks 32) may divert radially outward from the outer diameter of the pancreatic stent 26 as the wires 38 cross over or intersect the peaks 32.

Once the polymer layer 36 is disposed over the expandable metal support structure 34, it will be appreciated that the high spots (radially outwardmost portions) formed in the one or more wires 38 and the one or more wires 40 at each location 42 will form one of the peaks 32 (FIG. 2) that form part of each of the drainage features 28 (FIG. 2) therebetween. The peaks 32 defining the drainage features 28 therebetween, may extend helically around the circumference of the expandable metal support structure 34, for example. The expandable metal support structure 34 may be formed using any suitable technique. In some embodiments, the expandable metal support structure 34 may be formed by winding the one or more wires 38 and the one or more wires 40 onto a mandrel that is configured to provide the aforementioned high spots or radially outward extending peaks 32.

Figure 4:
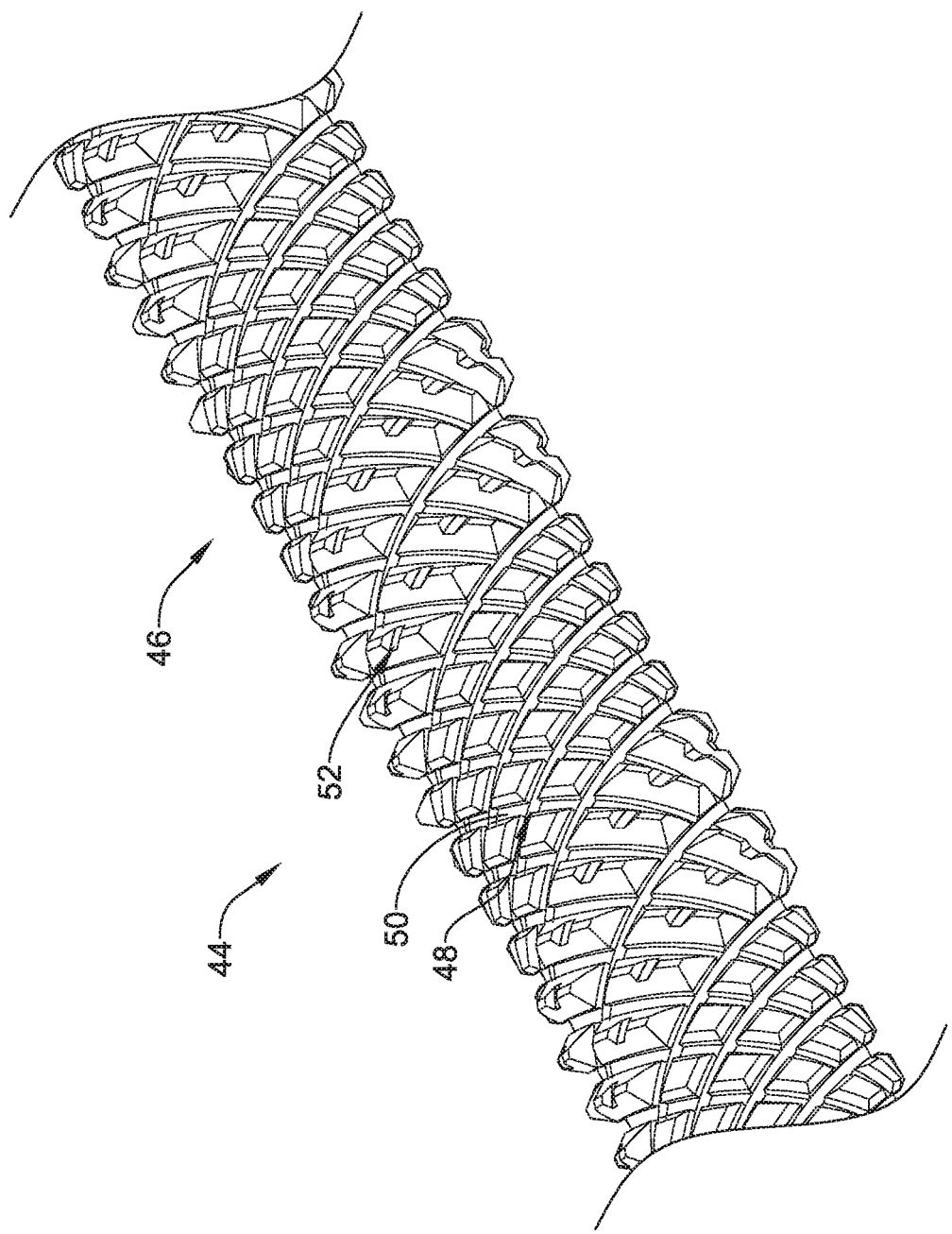
FIG. 4 is a schematic illustration of a mandrel useful in forming the metal framework of FIG. 3, in accordance with an embodiment of the disclosure.

FIG. 4 illustrates a mandrel 44 having an outer surface 46 that may be used to facilitate formation of the expandable metal support structure 34. A plurality of grooves 48, corresponding to the one or more wires 38, extend helically in a first direction around the circumference of the mandrel 44. A plurality of grooves 50, corresponding to the one or more wires 40, extend helically in a second direction around the circumference of the mandrel 44. The second direction being opposite the first direction. High spots 52 (i.e., portions of the mandrel 44 extending radially outward from the remainder of the mandrel 44) periodically interrupt the plurality of grooves 48. For example, high spots 52 of the mandrel 44 may include a groove having a base which is radially outward from the base of adjacent grooves and/or intersecting grooves formed in the mandrel 44. As the one or more wires 38 are wrapped around the mandrel 44 in the first direction, following the plurality of grooves 48, the one or more wires 38 will rise up over the high spots 52 formed in the mandrel 44, resulting in portions of the one or more wires 38 extending radially outward further than the remaining portions of the one or more wires 38. Additionally or alternatively, when the one or more wires 40 are wrapped around the mandrel 44 in the second direction, they will rise up over the high spots 52 formed in the mandrel 44, resulting in portions of the one or more wires 40 extending radially outward further than the remaining portions of the one or more wires 40, which may form the peaks 32.

It can be seen from FIG. 4, that a high spot 52 on the mandrel 44 may be located between adjacent wires 38 helically wound in the opposite helical direction as the peaks 32, while a wire 40 helically wound in the same helical direction as the peaks 32 may be located to follow a discontinuous groove formed in a helical arrangement of the high spots 52 circumferentially around the mandrel 44, with adjacent wires 40 located in grooves on either side of the helical arrangement of high spots 52.

Once the expandable metal support structure 34 has been formed, it may be removed from the mandrel 44 by applying a compressive axial force to the expandable metal support structure 34 to shorten its length and thus increase its diameter. In some embodiments, removal of the expandable metal support structure 34 may be achieved by utilizing shape memory properties to increase the diameter of the expandable metal support structure 34.

The polymer layer 36 may be formed of any suitable polymeric material. In some embodiments, the polymer layer 36 is formed of a biocompatible material such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like In some embodiments, the polymer layer 36 may be coated onto the expandable metal support structure 34 such as during a spray coating or dip coating process. In some embodiments, the polymer layer 36 may be formed over the expandable metal support structure 34 by stretching a polymeric sleeve over the expandable metal support structure 34.

The polymer layer 36 may conform to the contour of the expandable metal support structure 34, and thus may exhibit a non-uniform outer surface consequent the high-low pattern formed in the expandable metal support structure 34. The non-uniform outer surface of the polymer layer 36 may, at least in part, define the plurality of drainage features 28.

In some embodiments, the expandable metal support structure 34 may be formed from any desired material, such as a biocompatible material including biostable, bioabsorbable, biodegradable or bioerodible materials. For instance, the expandable metal support structure 34 may be formed of a metallic material. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

In some embodiments, the expandable metal support structure 34 may include one or more metals. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

Those skilled in the art will recognize that aspects of the present disclosure may be manifested in a variety of forms other than the specific embodiments described and contemplated herein. Accordingly, departure in form and detail may be made without departing from the scope of the present disclosure as described in the appended claims.

What is claimed is:

1. A mandrel for forming an expandable stent structure, comprising:
   a plurality of projections extending radially outward defining:
      a plurality of first grooves extending helically in a first direction around a circumference of the mandrel, the plurality of first grooves defining a first base; and
      a plurality of second grooves extending helically in a second direction around the circumference of the mandrel, the plurality of second grooves defining a second base;
   wherein the second direction is opposite the first direction;
   wherein the plurality of projections includes a plurality of taller projections having grooves formed therein defining a raised base that is disposed radially outward from the first base.

2. The mandrel of claim 1, wherein the raised base is disposed radially outward from the second base.

3. The mandrel of claim 1, wherein the plurality of taller projections are disposed along at least a portion of the mandrel.

4. The mandrel of claim 1, wherein the grooves of the plurality of taller projections extend helically along the mandrel in the first direction.

5. The mandrel of claim 1, wherein the plurality of taller projections extend radially outward farther than a remainder of the mandrel.

6. The mandrel of claim 1, wherein one or more first wires are wrapped around the mandrel in the first direction, the one or more first wires pass over the plurality of taller projections resulting in portions of the one or more first wires extending radially outward further than remaining portions of the one or more first wires.

7. A method of forming an expandable stent structure, comprising:
   winding one or more first wires around a circumference of a mandrel in a first direction, wherein the mandrel includes:
      a plurality of projections extending radially outward defining:
         a plurality of first grooves extending helically in the first direction around the circumference of the mandrel, the plurality of first grooves defining a first base; and
         a plurality of second grooves extending helically in a second direction around the circumference of the mandrel, the plurality of second grooves defining a second base;
      wherein the plurality of projections includes a plurality of taller projections having grooves formed therein defining a raised base that is disposed radially outward from the first base;
   winding one or more second wires around the circumference of the mandrel in the second direction;
   wherein the one or more first wires are interwoven with the one or more second wires;
   wherein at least a portion of the one or more first wires are wound around the circumference of the mandrel within the plurality of first grooves and the grooves of the plurality of taller projections.

8. The method of claim 7, wherein as the one or more first wires are wound around the mandrel in the first direction, the one or more first wires pass over the plurality of taller projections resulting in portions of the one or more first wires extending radially outward further than remaining portions of the one or more first wires.

9. The method of claim 7, wherein as the one or more second wires are wound around the mandrel in the second direction, the one or more second wires pass over the plurality of taller projections resulting in portions of the one or more second wires extending radially outward further than remaining portions of the one or more second wires.

10. The method of claim 7, wherein as the one or more second wires are wound around the mandrel in the second direction, the one or more second wires cross over the one or more first wires extending between adjacent taller projections resulting in portions of the one or more second wires extending radially outward further than remaining portions of the one or more second wires.

11. The method of claim 7, wherein the plurality of taller projections are disposed along at least a portion of the mandrel.

12. The method of claim 7, wherein the grooves of the plurality of taller projections extend helically along the mandrel in the first direction.

13. The method of claim 7, wherein the plurality of taller projections extend radially outward farther than a remainder of the projections of the mandrel.

14. The method of claim 7, wherein the raised base is disposed radially outward from the second base.

15. The method of claim 7, wherein at least a portion of the one or more second wires are wound around the circumference of the mandrel within the plurality of second grooves.

16. A mandrel for forming an expandable stent structure, comprising:
- a plurality of projections extending radially outward defining:
  - a plurality of first grooves extending helically in the first direction around the circumference of the mandrel, the plurality of first grooves defining a first base; and
  - a plurality of second grooves extending helically in a second direction around the circumference of the mandrel, the plurality of second grooves defining a second base;
- wherein some of the projections are taller projections having grooves formed across an outward facing surface thereof, each groove of the taller projections defining a raised base that is disposed radially outward from the first base and the second base;
- wherein one or more first wires wrapped around the mandrel in the first direction pass over the taller projections resulting in portions of the one or more first wires extending radially outward further than remaining portions of the one or more first wires.

17. The mandrel of claim 16, wherein the taller projections extend radially outward farther than a remainder of the plurality of projections of the mandrel.

18. The mandrel of claim 16, wherein one or more second wires wrapped around the mandrel in the second direction pass under the one or more first wires disposed in the plurality of first grooves immediately adjacent the taller projections and pass over the one or more first wires disposed in the grooves of the taller projections.

* * * * *